United States Patent [19]
Pisarik

[11] Patent Number: 6,024,697
[45] Date of Patent: Feb. 15, 2000

[54] MULTI-BLADED SPECULUM FOR DILATING A BODY CAVITY

[76] Inventor: Paul Pisarik, 4154 W. Corona Dr., Chandler, Ariz. 85226-7222

[21] Appl. No.: 09/228,217

[22] Filed: Jan. 11, 1999

[51] Int. Cl.[7] .................................................. A61M 29/00
[52] U.S. Cl. ........................................... 600/224; 600/214
[58] Field of Search ................... 600/224, 231, 600/233, 220, 210, 214

[56] References Cited

U.S. PATENT DOCUMENTS

| | | |
|---|---|---|
| 55,511 | 6/1866 | Leutz . |
| 151,228 | 5/1874 | Knaffl . |
| 350,721 | 10/1886 | Cooper . |
| 351,548 | 10/1886 | Watson . |
| 361,087 | 4/1887 | Schenck . |
| 447,761 | 3/1891 | Clough ..................................... 600/224 |
| 579,625 | 3/1897 | Willbrandt . |
| 605,547 | 6/1898 | Holland . |
| 639,444 | 12/1899 | Scheerer . |
| 658,669 | 9/1900 | Morrow . |
| 761,821 | 7/1904 | Clark et al. . |
| 786,457 | 4/1905 | McGinnis . |
| 977,489 | 12/1910 | Unruh ..................................... 600/224 |
| 1,014,799 | 1/1912 | Arthur . |
| 1,018,868 | 2/1912 | Breneman . |
| 1,194,319 | 8/1916 | Pretts . |
| 1,500,227 | 7/1924 | Breneman . |
| 1,614,065 | 1/1927 | Guttmann . |
| 1,633,443 | 6/1927 | Frangedakis ............................. 600/224 |
| 1,919,120 | 7/1933 | O'Connor et al. ...................... 600/223 |
| 2,083,573 | 6/1937 | Morgan . |
| 2,374,863 | 5/1945 | Guttmann . |
| 3,030,947 | 4/1962 | Engelbert . |
| 3,176,682 | 4/1965 | Wexler . |
| 3,509,873 | 5/1970 | Karlin et al. . |
| 3,709,215 | 1/1973 | Richmond . |
| 3,716,047 | 2/1973 | Moore et al. . |
| 3,853,120 | 12/1974 | Batista . |
| 5,081,983 | 1/1992 | Villalta et al. . |
| 5,183,032 | 2/1993 | Villalta et al. . |
| 5,400,774 | 3/1995 | Villalta et al. ........................... 600/224 |
| 5,505,690 | 4/1996 | Patton et al. ............................ 600/210 |
| 5,509,893 | 4/1996 | Pracas ..................................... 600/224 |
| 5,868,668 | 2/1999 | Weiss ...................................... 600/224 |
| 5,885,210 | 3/1999 | Cox ......................................... 600/224 |

*Primary Examiner*—Paul J. Hirsch

[57] ABSTRACT

A speculum for dilating a body cavity with at least three blades, twice as many supporting members, a rachet mechanism between pairs of directly connected supporting members, and a light source receptacle located on one of the blades with a curved plastic track at the base of the receptacle to transmit light from a removable, commercially available, light source into the cavity created by the speculum. Two of the supporting members, besides helping to move the blades from a closed to an open position and back, can also pivot anteriorly.

26 Claims, 11 Drawing Sheets

MULTI-BLADED SPECULUM FOR DILATING A BODY CAVITY

BACKGROUND

1. Field of Invention

This invention relates to a medical device, specifically a device to dilate and retract the walls of a body cavity.

2. Description of Prior Art

Traditional devices for dilating body cavities include medical or surgical instruments known variously as specula, dilators, or retractors. The term speculum or dilator is usually used to designate a device, which enlarges, dilates, allows easier access to, or better visualization of an existing body cavity, such as a vagina, ear, nose, or rectum. The term retractor, on the other hand, is usually reserved to designate a device used during a surgical procedure where an incision is made into the body and a temporary opening into the body is made. The walls of the incised portion of the body are then held apart by means of retractors so that the surgeon can operate inside this temporary opening. For the purposes of this patent application, the term speculum will be used to refer to a device that can perform not only the functions of a speculum or dilator, but that also of a retractor.

The specula, that have been patented in the past, can be placed in one of the following categories:

1. A single-bladed speculum that either has to be
   (a) held in place by an assistant,
   (b) attached to the body in some manner (U.S. Pat. No. 3,853,120 to Batista, U.S. Pat. No. 3,709,215 to Richmond), or
   (c) held in place by gravity.

2. The traditional "duck-billed" speculum having two opposed concavoconvex blades (U.S. Pat. No. 3,716,047 to Moore et al, among many others).

Frequently the handle and lower blade are integral parts of the same piece of material. The upper blade is pivotally attached to a sliding member that runs vertically and is attached to the proximal end (that closest to the operator) of the lower blade/handle complex. The upper speculum blade can be adjusted vertically to enlarge the proximal opening of the speculum. Then, after this is fixed in place, the speculum can be opened or diverged. The proximal end of the upper blade that is pivotally fixed to the lower blade/handle complex then remains the same vertical distance from the proximal end of the lower blade whereas the distal portion of the upper blade (that furthest from the operator) moves vertically from the distal portion of the lower blade.

At full divergence, the longitudinal axes of the upper and lower blades of the "duck-billed" speculum can be thought to meet at a point outside the body cavity, and therefore can be likened to the radii of a circle. Thus, the movement of the upper blade with respect to the lower blade can be said to be radial.

Parallel movement of the blades with respect to each other, of certain other specula, can be said to occur when the longitudinal axes of the upper and lower blades are parallel during divergence and convergence. Thus, the distance between the blades at the proximal and distal ends is always the same.

3. A three-bladed speculum in which, during divergence or convergence, the blades either move:
   (a) parallel to each other (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 579,625 to Willbrandt, U.S. Pat. No. 1,194,319 to Pretts, U.S. Pat. No. 605,547 to Holland, U.S. Pat. No. 1,014,799 to Arthur, U.S. Pat. No. 3,030,947 to Engelbert, U.S. Pat. No. 3,176,682 to Wexler, U.S. Pat. No. 3,509,873 to Karlin et al), or
   (b) radially to each other (U.S. Pat. No. 639,444 to Scheerer, U.S. Pat. No. 658,669 to Morrow, U.S. Pat. No. 786,457 to McGinnis).

4. A four-bladed speculum in which, during divergence and convergence, the blades either move:
   (a) parallel to each other (U.S. Pat. No. 151,228 to Knaffl, U.S. Pat. No. 977,489 to Von Unruh, U.S. Pat. No. 1,018,868 to Breneman, U.S. Pat. No. 1,500,227 to Breneman, U.S. Pat. No. 2,083,573 to Morgan, U.S. Pat. No. 5,183,032 to Villalta et al, U.S. Pat. No. 5,081,983 to Villalta et al), or
   (b) radially to each other (U.S. Pat. No. 55,511 to Leutz, U.S. Pat. No. 5,509,893 to Pracas).

5. A five-or-more-bladed speculum (U.S. Pat. No. 5,505,690 to Patton et al).

The disadvantages of the specula that have been previously patented can be summarized as follows:

1. Conventional specula are manufactured of surgical steel that need to be sterilized after each use to prevent cross contamination between patients (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 579,625 to Willbrandt, U.S. Pat. No. 1,194,319 to Pretts, U.S. Pat. No. 605,547 to Holland, U.S. Pat. No. 1,014,799 to Arthur, U.S. Pat. No. 3,030,947 to Engelbert, U.S. Pat. No. 3,176,682 to Wexler, U.S. Pat. No. 3,509,873 to Karlin et al, U.S. Pat. No. 639,444 to Scheerer, U.S. Pat. No. 658,669 to Morrow, U.S. Pat. No. 786,457 to McGinnis, U.S. Pat. No. 151,228 to Knaffl, U.S. Pat. No. 977,489 to Von Unruh, U.S. Pat. No. 1,018,868 to Breneman, U.S. Pat. No. 1,500,227 to Breneman, U.S. Pat. No. 2,083,573 to Morgan, U.S. Pat. No. 5,183,032 to Villalta et al, U.S. Pat. No. 5,081,983 to Villalta et al, U.S. Pat. No. 55,511 to Leutz).

Such sterilization is time consuming and costly necessitating equipment, labor, and quality control to ensure adequate cleaning and sterilization.

Furthermore, steel devices take on the temperature of the ambient air, which in most circumstances, is 20 + degrees Fahrenheit colder than a patient's body temperature.

Typical examinations of body cavities in a conscious patient ordinarily are anxiety provoking. Accordingly, the added shock of a cold surgical instrument applied to the tissue of the patient heightens the anxiousness of the patient. Furthermore, anxious patients may have more tightly tensed muscles that impede the dilation of the body cavity being examined. Thus, they are that much more uncomfortable. The physical examination of the body cavity is thus hampered and slowed.

2. The actual divergence and convergence of the blades of many specula are accomplished by applying forces that aren't applied directly perpendicularly to the walls of the body cavity being dilated (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 1,014,799 to Arthur, U.S. Pat. No. 3,030,947 to Engelbert, U.S. Pat. No. 658,669 to Morrow, U.S. Pat. No. 2,083,573 to Morgan, U.S. Pat. No. 5,509,893 to Pracas).

Applying such indirect forces means that a greater total force is needed, thus making it harder to operate such specula and increasing operator fatigue.

3. The actual mechanism that holds the blades in divergence in many specula (and that needs to be undone for convergence) involves turning a screw or wingnut a number of revolutions (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 1,194,319 to Pretts, U.S. Pat. No. 605,547 to Holland, U.S. Pat. No. 1,014,799 to Arthur, U.S. Pat. No. 3,030,947 to Engelbert, U.S. Pat. No. 3,509,873 to Karlin et al, U.S. Pat. No. 639,444 to Scheerer, U.S. Pat. No. 658,669 to Morrow, U.S. Pat. No. 151,228 to Knaffl, U.S. Pat. No. 977,489 to Von Unruh, U.S. Pat. No. 5,183,032 to Villalta et al, U.S. Pat. No. 5,081,983 to Villalta et al, U.S. Pat. No. 55,511 to Leutz).

Such a mechanism takes an undue amount of time to both set up and take down.

4. Many specula, as designed, have blades that substantially obstruct the view of the walls of the body cavity being dilated or totally encircle the body cavity being dilated (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 605,547 to Holland, U.S. Pat. No. 1,014,799 to Arthur, U.S. Pat. No. 3,030,947 to Engelbert, U.S. Pat. No. 3,176,682 to Wexler, U.S. Pat. No. 639,444 to Scheerer, U.S. Pat. No. 658,669 to Morrow, U.S. Pat. No. 786,457 to McGinnis, U.S. Pat. No. 151,228 to Knaffl, U.S. Pat. No. 977,489 to Von Unruh, U.S. Pat. No. 2,083,573 to Morgan, U.S. Pat. No. 5,183,032 to Villalta et al, U.S. Pat. No. 5,081,983 to Villalta et al, U.S. Pat. No. 55,511 to Leutz, U.S. Pat. No. 5,509,893 to Pracas).

Such a design does not allow operations to be done on the walls of the body cavity being dilated (such as repair of episiotomies or vaginal tears just after delivery) or outside the body cavity (such as repairs of the perineum or rectum after delivery). Some of the devices could perhaps be rotated to allow for this. However, this might render the speculum non-self-retaining and thus require an assistant to hold it in place.

5. Most specula in the prior art, do not have a mechanism to channel light directly into the interior of the cavity they create (U.S. Pat. No. 350,721 to Cooper, U.S. Pat. No. 351,548 to Watson, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 579,625 to Willbrandt, U.S. Pat. No. 1,194,319 to Prefts, U.S. Pat. No. 605,547 to Holland, U.S. Pat. No. 1,014,799 to Arthur, U.S. Pat. No. 3,030,947 to Engelbert, U.S. Pat. No. 3,176,682 to Wexler, U.S. Pat. No. 3,509,873 to Karlin et al, U.S. Pat. No. 639,444 to Scheerer, U.S. Pat. No. 658,669 to Morrow, U.S. Pat. No. 786,457 to McGinnis, U.S. Pat. No. 151,228 to Knaffl, U.S. Pat. No. 977,489 to Von Unruh, U.S. Pat. No. 1,018,868 to Breneman, U.S. Pat. No. 1,500,227 to Breneman, U.S. Pat. No. 2,083,573 to Morgan, U.S. Pat. No. 5,183,032 to Villalta et al, U.S. Pat. No. 5,081,983 to Villalta et al, U.S. Pat. No. 55,511 to Leutz, U.S. Pat. No. 5,509,893 to Pracas, U.S. Pat. No. 5,505,690 to Patton et al).

Most operators of specula, and others knowledgeable in the art, realize that having a speculum with a mechanism to channel light directly into the interior of a body cavity provides excellent illumination and visualization of that body cavity. Specula, that have no such mechanism, require a light coming from outside the body cavity. This light, besides not being as bright as that light from the above mechanism, can be blocked by the operator, his or her assistant, or another instrument, and usually does not illuminate a part of the vaginal wall since it is coming at an angle from outside the vagina. Excellent illumination is critical to making accurate diagnoses and for operating in the body cavity itself.

6. Many of the more-than-two-bladed specula do not allow the vertical opening of the blades of the speculum to be made independently from the horizontal (U.S. Pat. No. 350,721 to Cooper, U.S. Pat. No. 361,087 to Schenck, U.S. Pat. No. 761,821 to Clark et al, U.S. Pat. No. 1,614,065 to Guttmann, U.S. Pat. No. 2,374,863 to Guttmann, U.S. Pat. No. 579,625 to Willbrandt, U.S. Pat. No. 1,014,799 to Arthur, U.S. Pat. No. 3,030,947 to Engelbert, U.S. Pat. No. 639,444 to Scheerer, U.S. Pat. No. 786,457 to McGinnis, U.S. Pat. No. 977,489 to Von Unruh, U.S. Pat. No. 1,018,868 to Breneman, U.S. Pat. No. 1,500,227 to Breneman, U.S. Pat. No. 2,083,573 to Morgan, U.S. Pat. No. 5,183,032 to Villalta et al, U.S. Pat. No. 5,081,983 to Villalta et al, U.S. Pat. No. 55,511 to Leutz, U.S. Pat. No. 5,509,893 to Pracas, U.S. Pat. No. 5,505,690 to Patton et al).

This mechanism of divergence and convergence does not allow putting differential tension on the walls of the vagina so that the vaginal wall between some blades is taut and between other blades is relaxed. It also does not allow a way for the speculum to be adapted to the anatomic variability that exists among patients.

7. All of the specula, in which the blades move radially, have a fixed opening to the specula (U.S. Pat. No. 639,444 to Scheerer, U.S. Pat. No. 658,669 to Morrow, U.S. Pat. No. 786,457 to McGinnis, U.S. Pat. No. 55,511 to Leutz, U.S. Pat. No. 5,509,893 to Pracas).

This fixed opening restricts access to the opening of the body cavity and lessens visibility to the area to be examined, treated, or on which the surgery needs to be done.

8. Some older devices were designed to be made out of wire (U.S. Pat. No. 658,669 to Morrow, U.S. Pat. No. 151,228 to Knaffl).

The wire specula cannot adequately hold back the walls of whatever body cavity is being dilated.

9. Some specula are not self-retaining (U.S. Pat. No. 1,018,868 to Breneman, U.S. Pat. No. 1,500,227 to Breneman, U.S. Pat. No. 5,183,032 to Villalta et al, U.S. Pat. No. 5,081,983 to Villalta et al).

Non-self-retaining specula require an additional operator to hold such an instrument in place.

In particular, regarding postpartum vaginal examinations, no commercially successful speculum is available that adequately assists in the examination and repair of the cervix or vagina.

What practitioners of the art commonly do now, is to have an assistant hold a wide, single-bladed speculum up against the upper vaginal wall to get that tissue retracted as well as to separate the lateral (side) vaginal walls by draping them over the edges of the single-bladed speculum in this area. Then the practitioner uses his or her nondominant hand to depress the lower vaginal wall to try to get a visual inspection of the vagina and cervix. A weighted vaginal speculum cannot be used since it would hinder examination of the lower vaginal wall for tears and in the repair of the same.

To repair an episiotomy or vaginal tear, the operator needs to continue depressing the effected vaginal wall with their nondominant hand, putting the index finger on one side of the apex of the defect and the third digit on the opposite side. Then using the dominant hand with a suture on a needle holder, they go to the apex of the defect and, going through the vaginal tissue, anchor the first stitch. Then they have to stop depressing the vaginal wall, remove their nondominant hand, and tie the first knot in the suture. Their nondominant hand then again depresses the effected vaginal wall, with the second and third fingers placed on opposite sides of the vaginal defect. The dominant hand then continues suturing the defect until the perineum is reached.

Sometimes even though one uses an anterior blade to retract the upper vaginal wall and the nondominant hand or even a weighted speculum for the lower vaginal wall (after any defects are sutured), one still cannot visualize the cervix because of the redundancy of the postpartum vaginal tissue. Therefore, many times the cervix needs to be inspected by feel. If a defect is felt that needs to be fixed, two ring forceps are placed on either side of the cervical tear. The ring forceps are then pulled toward the operator with the nondominant hand until the cervical tear is visible and then it is sutured.

One can see that this process is very laborious, leading to operator and patient fatigue. It is also quite time consuming, expending valuable operator, support personnel, and delivery room time. It is also prone to incorrect or missed diagnoses and thus incorrect treatment. Taking a long time to diagnose and suture a defect in the cervix or vagina that is bleeding or diagnose and remove a retained piece of placenta, can lead to excessive bleeding. This could cause the patient to be in shock or be severely anemic, either one of which could require a blood transfusion.

OBJECTS AND ADVANTAGES

Accordingly, it is an object of the invention to provide a speculum that overcomes the drawbacks of the known devices especially as it relates (but not limited) to postpartum vaginal examination, diagnosis, and treatment. Additionally, several objects and advantages of the present invention are to provide a speculum:

(a) which is simple to use;
(b) which can dilate a body cavity quickly with the use of the two hands of one operator alone and can be collapsed as quickly;
(c) which, in a conscious patient, will lessen the anguish, discomfort, and possible psychological trauma caused by using conventional specula and/or manual techniques during operative procedures especially during postpartum vaginal examinations and vaginal and cervical defect repairs;
(d) which will decrease the overall time for examination, diagnosis, and surgical procedures involving dilatation of body cavities, such as the examination, diagnosis and repair of postpartum vaginal and cervical defects;
(e) where the blades of the speculum allow maximal visualization of the walls of the body cavity being dilated as well as the body cavity itself, thus maximizing the operative field;
(f) where the area surrounding the opening into the body cavity is left clear so that operations done on the surface of the body near the cavity are not obstructed or hampered, such as repair of perineal or rectal tears;
(g) where the blades can be manipulated in such a way that the shape of the final configuration of the speculum (and thus of the body cavity) can be in an almost limitless number of configurations;
(h) that has a mechanism to channel light directly into the interior of the body cavity from a removable light source whose location and associated electrical cord are above the operative field;
(i) that is self-retaining in the body cavity that it is dilating;
(j) that is made of a hard plastic-type material that temperature-wise is comfortable when applied to the skin or mucous membranes of a conscious patient;
(k) that is disposable and thus not needing sterilization;
(l) where the force to diverge the blades is applied directly to the walls of the body cavity thus conserving energy;
(m) which eliminates the need for using additional retractors (including the hand);
(n) having a tissue-spreading blade mechanism that can stretch the portions of the walls of the body cavity tautly that do not need to be operated on to keep them from obstructing the operator's operative field and yet leave the portions of the walls that do need attention and repair, relaxed;
(o) suited for use with other surgical instruments; and
(p) versatile enough to be used with a patient in any position especially as it relates to postpartum examination either on a delivery table with feet in stirrups or lying on a regular bed.

Still, further objects and advantages will become apparent from a consideration of the ensuing description and accompanying drawings.

REFERENCE NUMERALS IN DRAWINGS

Figure 1:
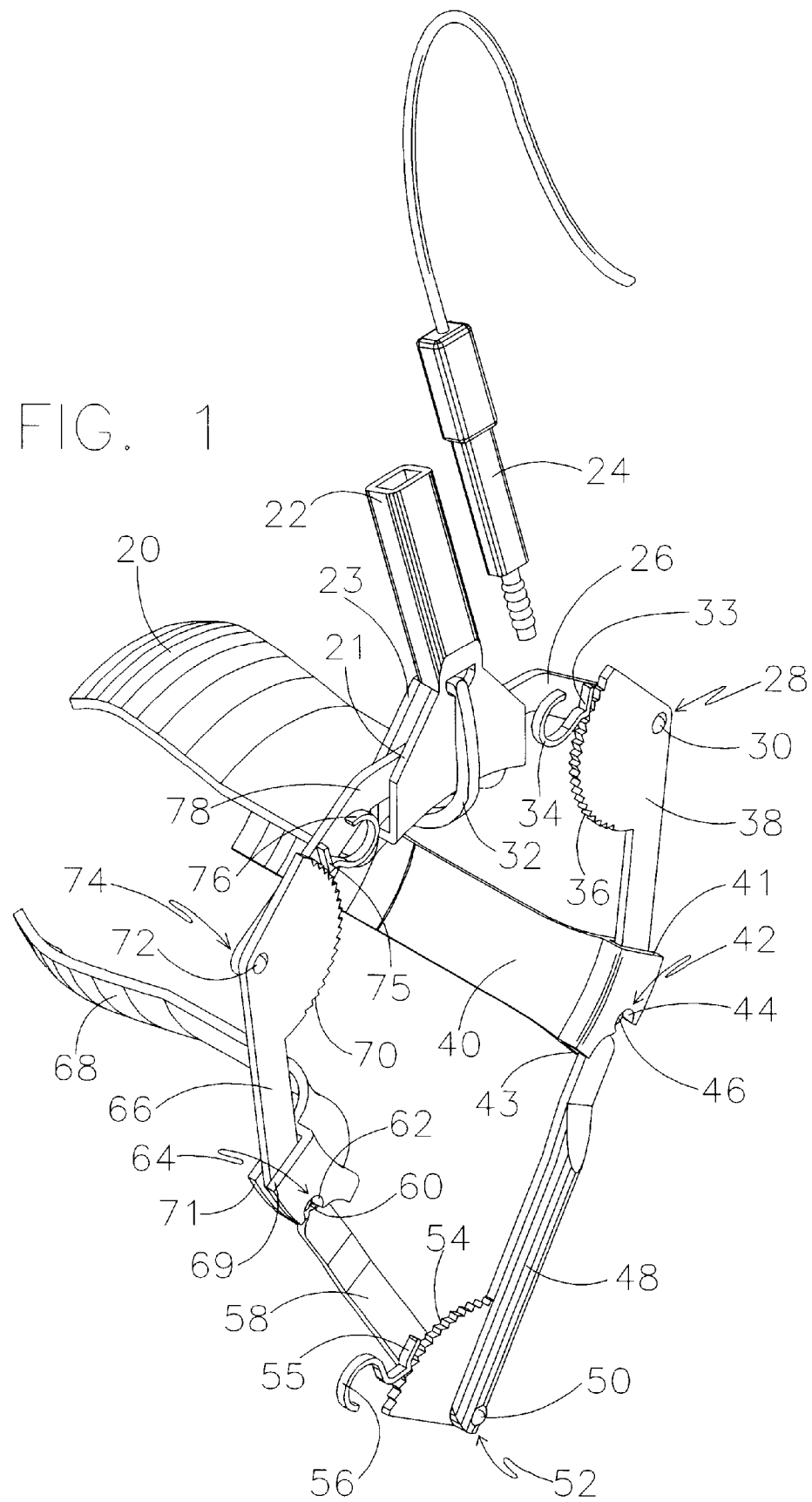
FIG. 1 is a perspective view of an opened speculum, also showing a commercially available light source.

Since the preferred embodiment of the speculum will be used in the postpartum setting with the patient facing the operator, designations of left and right are those of the patient's left and right. In other words, the side of the speculum that will be alongside the patient's left will be labeled as left (even though it will be on the operator's right).

20 top blade
21 anterior face of top blade
22 hollow receptacle for a light source/upper handle
23 posterior face of top blade
24 commercially available light source
26 left upper arm support
28 left elbow joint
30 bolt
32 curved light-transmitting plastic track
33 pawl 34 release ring
36 series of rachet teeth of left lower arm support
38 left lower arm support
40 left blade
41 anterior face of left blade
42 left ball-and-socket joint
43 posterior face of left blade
44 cutaway section of the anterior face of left blade for left ball-and-socket joint
46 ball portion of left leg support for left ball-and-socket joint
48 left leg support
50 bolt
52 hinge joint of left and right leg supports
54 series of rachet teeth of left leg support
55 pawl
56 release ring
58 right leg support
60 ball portion of right leg support for right ball-and-socket joint
62 cutaway section of anterior face of right blade for right ball-and-socket joint
64 right ball-and-socket joint
66 right lower arm support
68 right blade
69 anterior face of right blade
70 series of rachet teeth of right lower arm support
71 posterior face of right blade
72 bolt
74 right elbow joint
75 pawl
76 release ring
78 right upper arm support
80 series of gear teeth at medial end of right upper arm support
81 series of gear teeth at medial end of left upper arm support
82 cross-section of peg at medial end of right upper arm support
83 cross-section of peg at medial end of left upper arm support
84 cross-section of peg at medial end of left lower arm support
85 cross-section of peg at medial end of right lower arm support
86 partial cross-section of the ball portion of the left leg support
87 depression in posterior face of right blade
88 alternate left blade
89 alternate anterior face of left blade
90 alternate left lower arm support
91 alternate posterior face of left blade
92 alternate left leg support
94 alternate right leg support
96 alternate right lower arm support
97 alternate posterior face of right blade
98 alternate right blade
99 alternate anterior face of right blade
100 cross-section of peg at medial end of alternate left lower arm support
102 cross-section of peg at superior end of alternate left leg support
104 series of gear teeth at medial end of alternate left lower arm support
106 series of gear teeth at superior end of alternate left leg support
108 cross-section of peg at medial end of alternate right lower arm support
110 cross-section of peg at superior end of alternate right leg support
112 series of gear teeth at medial end of alternate right lower arm support
114 series of gear teeth at superior end of alternate right leg support
116 vaginal wall
118 dilated postpartum cervix
120 cervical tear
122 vaginal defect—episiotomy, or tear
124 rectum
126 contracted postpartum uterus Summary In accordance with the present invention, a speculum for dilating a body cavity with at least three blades, twice as many supporting members, a rachet mechanism between pairs of directly connected supporting members, and a light source receptacle located on one of the blades with a curved plastic track at the base of the receptacle to transmit light from a removable, commercially available, light source into the cavity created by the speculum. Two of the supporting members, besides helping to move the blades from a closed to an open position and back, can also pivot anteriorly.

Description of the Preferred Embodiment—FIGS. 1 to 7

Figure 2:
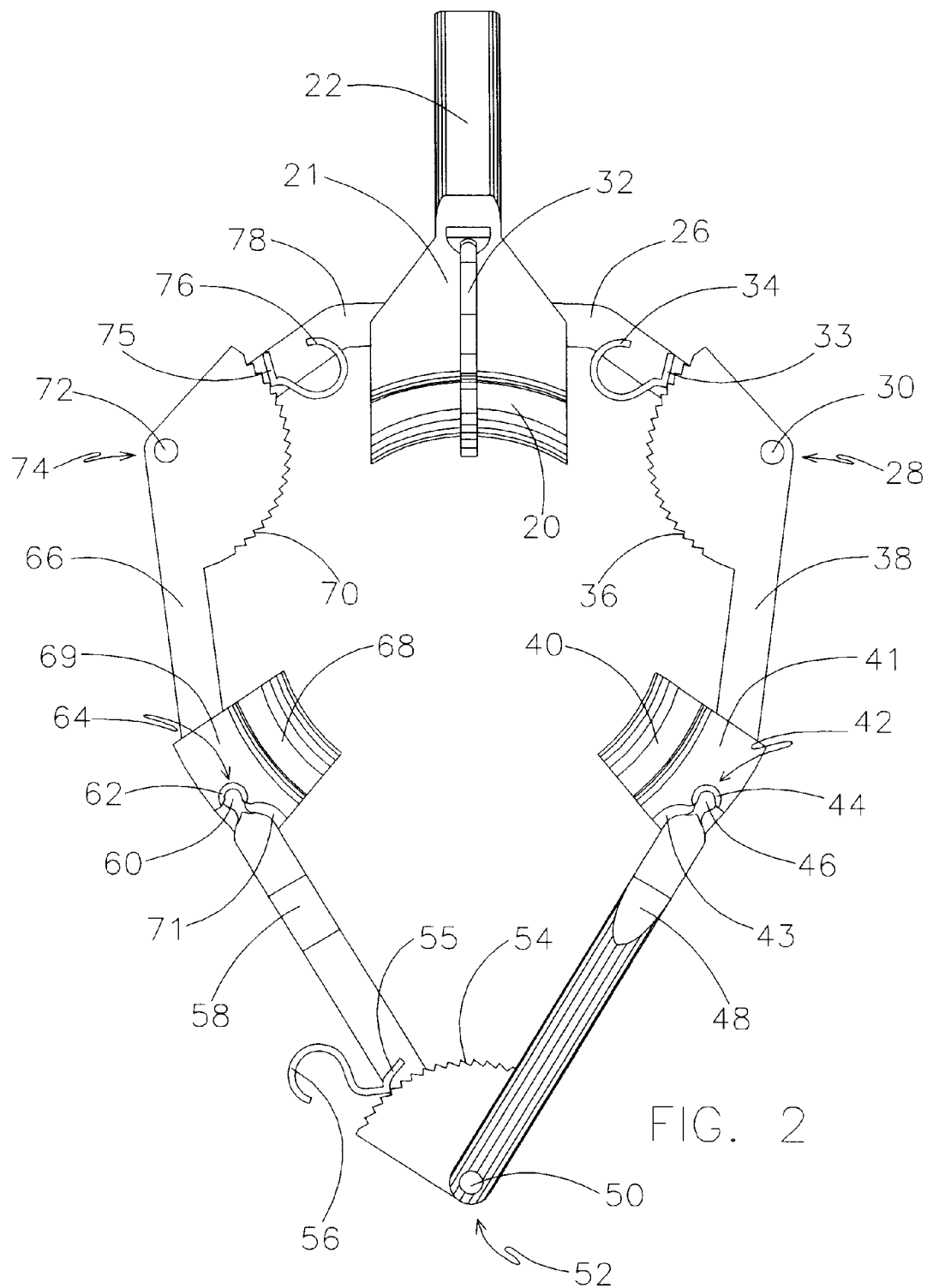
FIG. 2 is a frontal view of the speculum of FIG. 1.
Figure 3:
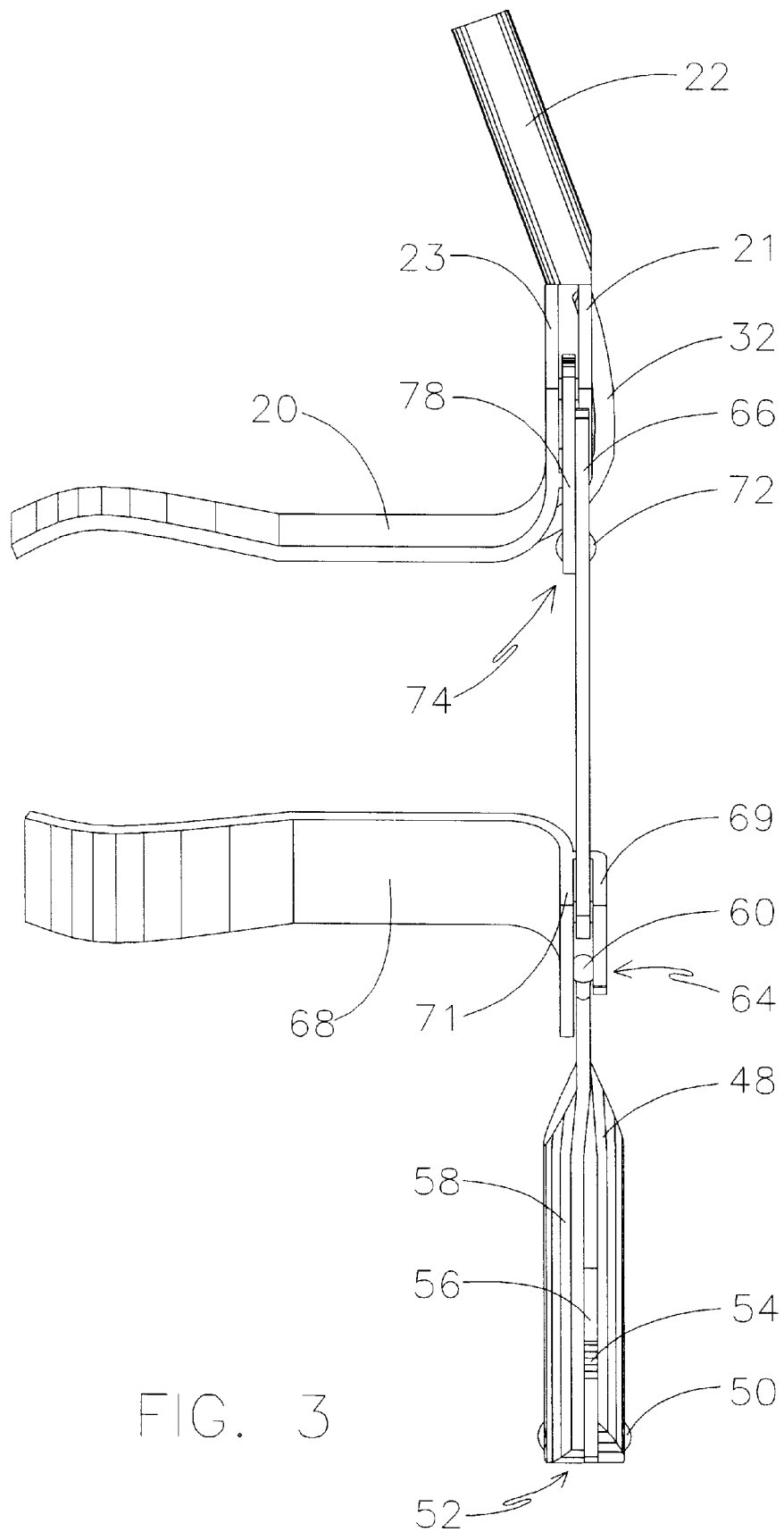
FIG. 3 is a side view of the speculum of FIG. 1.
Figure 4:
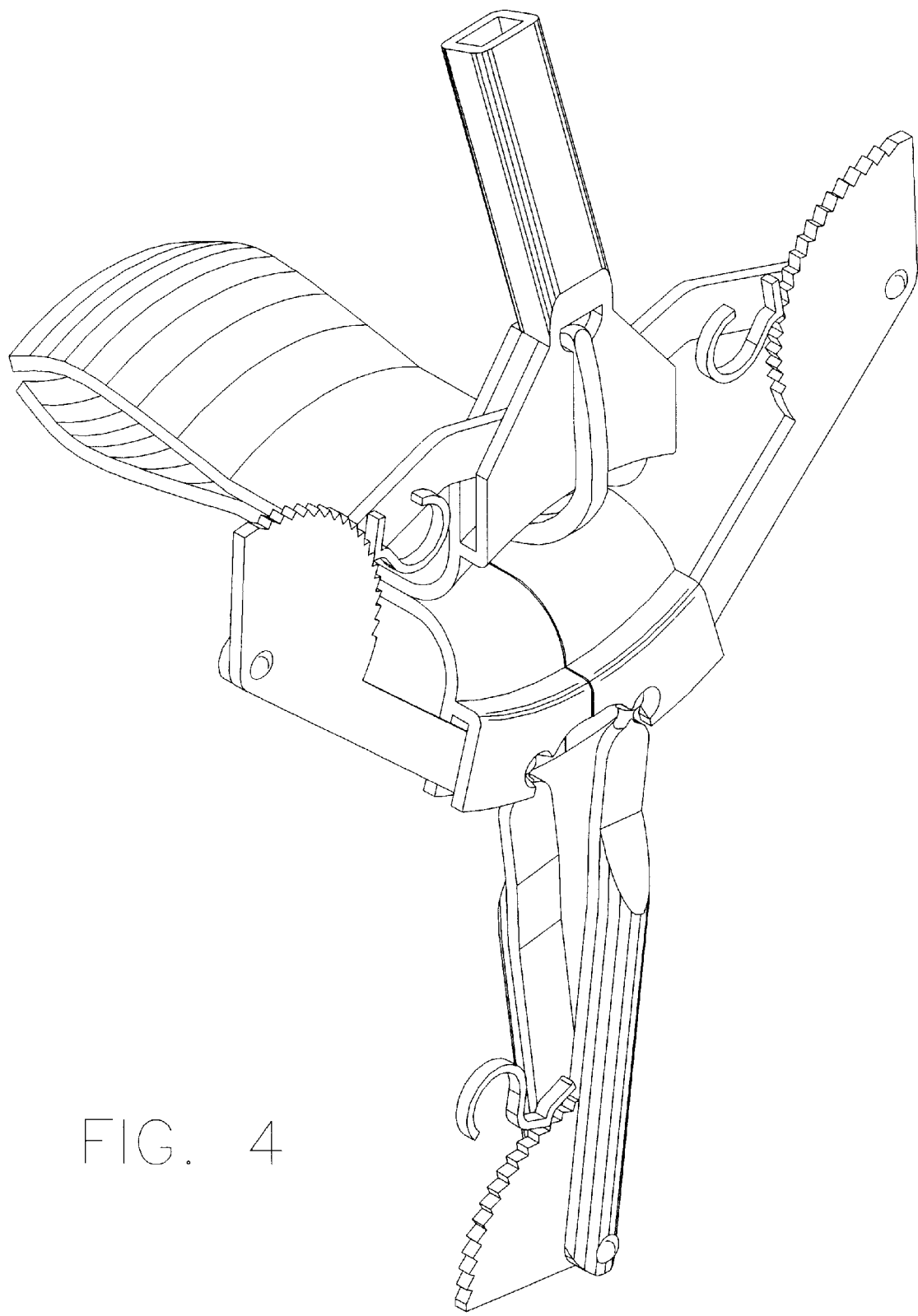
FIG. 4 is a perspective view of a closed speculum.
Figure 5:
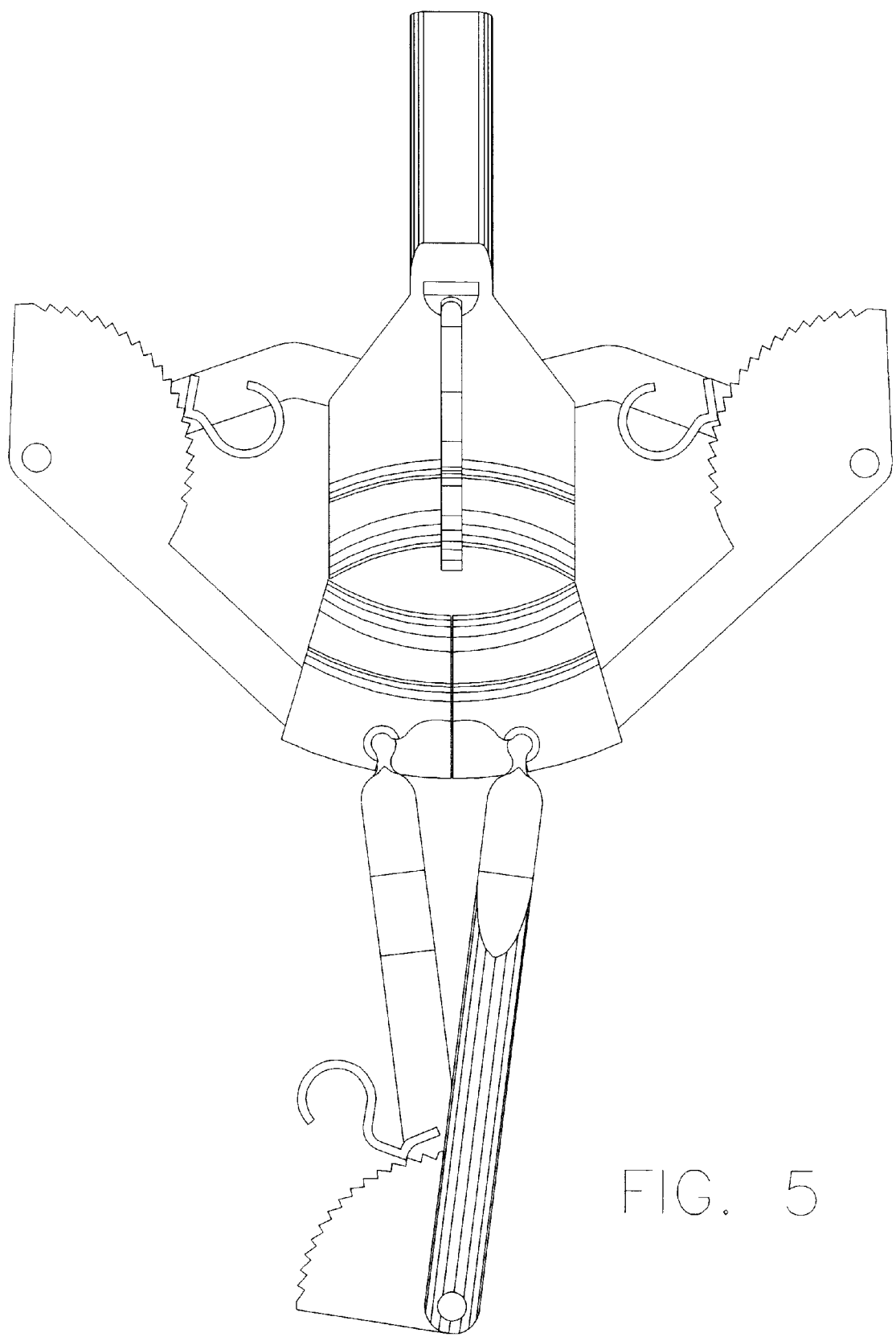
FIG. 5 is a frontal view of the speculum of FIG. 4.

The preferred embodiment of the open speculum of the present invention is illustrated in FIG. 1 (perspective view), FIG. 2 (frontal view), and FIG. 3 (side view). The preferred embodiment of a closed speculum is illustrated in FIG. 4 (perspective view), FIG. 5 (frontal view), and FIG. 6 (side view).

The major components of the speculum can be organized into the following categories:

the blades, the supporting arms, the connections between the supporting arms, the connections between the supporting arms and the blades, the illumination system, and the handles.

Blades

A blade is an elongated piece of material, preferably made of a clear hard plastic, with a slight curvature perpendicular to the long axis of the blade and concave to the cavity created by the speculum. The distal end of the blade has a slight curvature parallel to the long axis curved away from the cavity created by the speculum. The proximal end of the blade (the face) is bent 90 degrees to that long axis and directed to the outside of the speculum. The preferred embodiment has three blades—a top blade 20, a left blade 40, and a right blade 68.

FIGS. 1, 3, 4, and 6 show that the face of blade 20 actually consists of two surfaces, an anterior face 21 and a posterior face 23 connected to each other at the point where the blade has finished bending 90 degrees to the outside of the speculum. The face of blade 40 also consists of two surfaces, an anterior face 41 and a posterior face 43 connected to each other at the point where the blade has finished bending 90 degrees to the outside of the speculum. Finally the face of blade 68 consists of two surfaces, an anterior face 69 and a posterior face 71 connected to each other at the point where the blade has finished bending 90 degrees to the outside of the speculum.

The supporting arms are connected to the anterior and posterior faces in the space between the faces as will be described in detail below.

Supporting Arms

The preferred embodiment has six supporting members—a left upper arm support 26, a left lower arm support 38, a left leg support 48, a right leg support 58, a right lower arm support 66, and a right upper arm support 78.

Connections Between the Supporting Arms

The left upper arm support 26 is connected to the left lower arm support 38 by a bolt 30 that allows these two supports to pivot about each other, creating a left elbow joint 28. The portion of the left lower arm support 38 that is proximal to the left elbow joint 28, and that faces the inside of the speculum, is fan shaped. The edge of this fan has a series of rachet teeth 36 that are arranged in such a manner as to have a constant radius from bolt 30.

The left upper arm support 26 has a pawl 33 made of a more flexible plastic material that is attached at one end to the left upper arm support 26. The opposite end engages the series of rachet teeth 36. This series of rachet teeth 36 are biased in such a manner that the left upper arm support 26 can only be rotatably adjustable away from the left lower arm support 38, widening the angle between the two supports.

Attached to the end of the pawl 33 that engages the series of rachet teeth 36 is a release ring 34. When this is pulled medially, it disengages this end of the pawl 33 from the series of rachet teeth 36, allowing the left upper arm support 26 and the left lower arm support 38 to move back toward each other.

Similarly, the right upper arm support 78 is connected to the right lower arm support 66 by a bolt 72 that allows these two supports to pivot about each other, creating a right elbow joint 74. The portion of the right lower arm support 66 that is proximal to the right elbow joint 74, and that faces the inside of the speculum, is fan shaped. The edge of this fan has a series of rachet teeth 70 that are arranged in such a manner as to have a constant radius from bolt 72.

The right upper arm support 78 has a pawl 75 made of a more flexible plastic material that is attached at one end to the right upper arm support 78. The opposite end engages the series of rachet teeth 70. This series of rachet teeth 70 are biased in such a manner that the right upper arm support 78 can only be rotatably adjustable away from the right lower arm support 66, widening the angle between the two supports.

Attached to the end of the pawl 75 that engages the series of rachet teeth 70 is a release ring 76. When this is pulled medially, it disengages this end of the pawl 75 from the series of rachet teeth 70, allowing the right upper arm support 78 and the right lower arm support 66 to move back toward each other.

Finally, the left leg support 48 is connected to the right leg support 58 by a bolt 50 that allows these two supports to pivot about each other, creating a hinge joint of the left and right leg supports 52. The portion of the left leg support 48 that is proximal to the this hinge joint 52, and that faces the inside of the speculum, is fan shaped. The edge of this fan has a series of rachet teeth 54 that are arranged in such a manner as to have a constant radius from bolt 50.

The right leg support 58 has a pawl 55 made of a more flexible plastic material that is attached at one end to the right leg support 58. The opposite end engages the series of rachet teeth 54. This series of rachet teeth 54 are biased in such a manner that the right leg support 58 can only be rotatably adjustable away from the left leg support 48, widening the angle between the two supports.

Attached to the end of the pawl 55 that engages the series of rachet teeth 54 is a release ring 56. When this is rotated medially, it disengages this end of the pawl 55 from the series of rachet teeth 54, allowing the left leg support 48 and the right leg support 58 to move back toward each other.

Connections Between the Supporting Arms and the Blades

Figure 6:
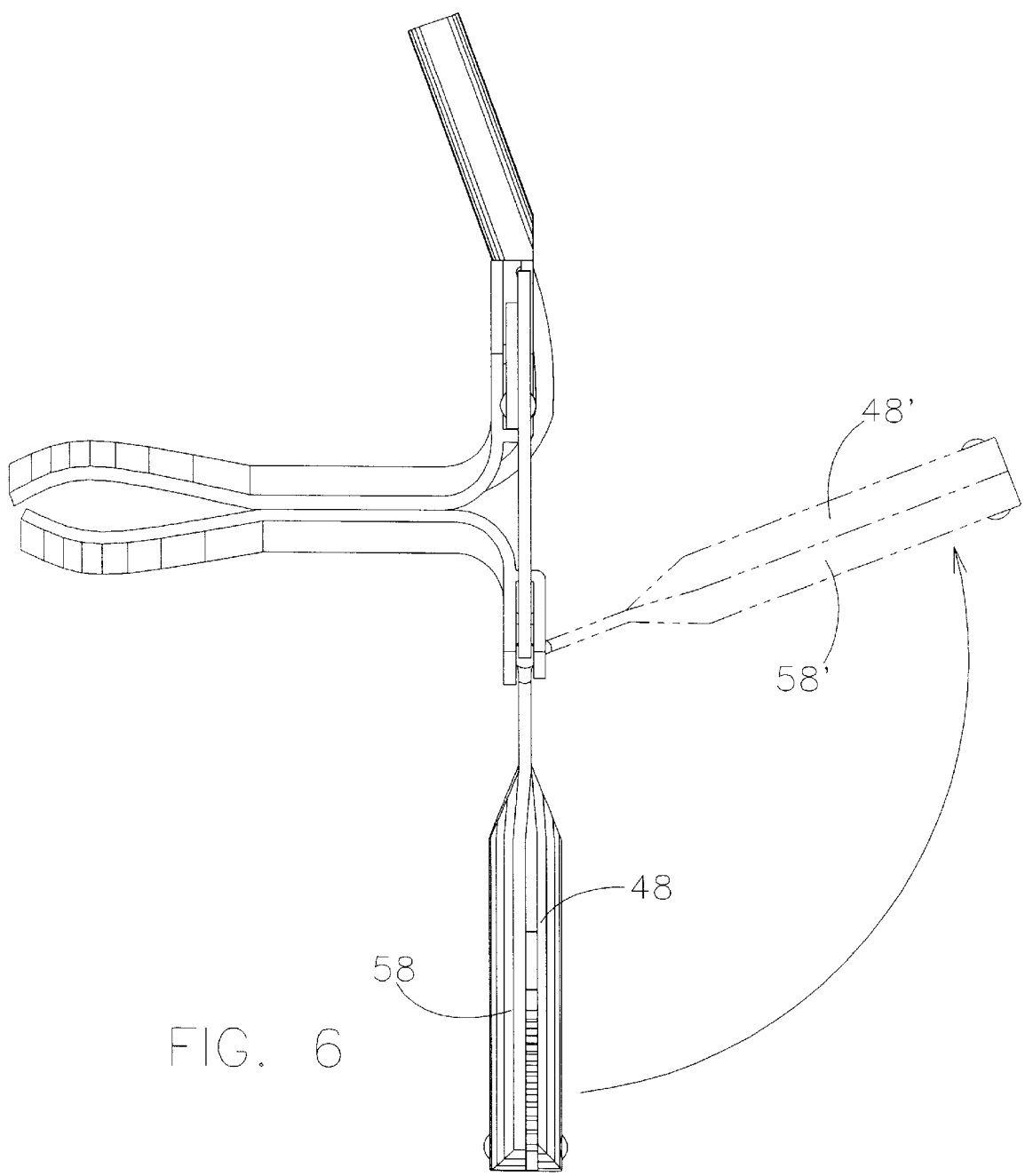
FIG. 6 is a side view of the speculum of FIG. 4, also showing the range through which the leg supports can travel toward the operator.

FIGS. 1, 2, 4, and 5 show that a left ball-and-socket joint 42 is composed of a ball and a socket. The "ball" is a ball portion of the left leg support 46. The socket is formed from a cutaway section of the anterior face of the left blade 44 just anterior and inferior to the ball portion of the left leg support 46 as well as a depression in the posterior face of the left blade 43 just posterior to the ball portion of the left leg support 46 (not shown for the posterior face 43). This not only allows the ball portion 46 (and thus the left leg support 48 itself to rotate medially and laterally in the plane between the anterior and posterior faces, but also allows the ball portion of the left leg support 46 to rotate anteriorly (FIG. 6). Thus the left leg support 48 can pivot in the direction of the arrow in FIG. 6 to a position 48'.

Figure 7:
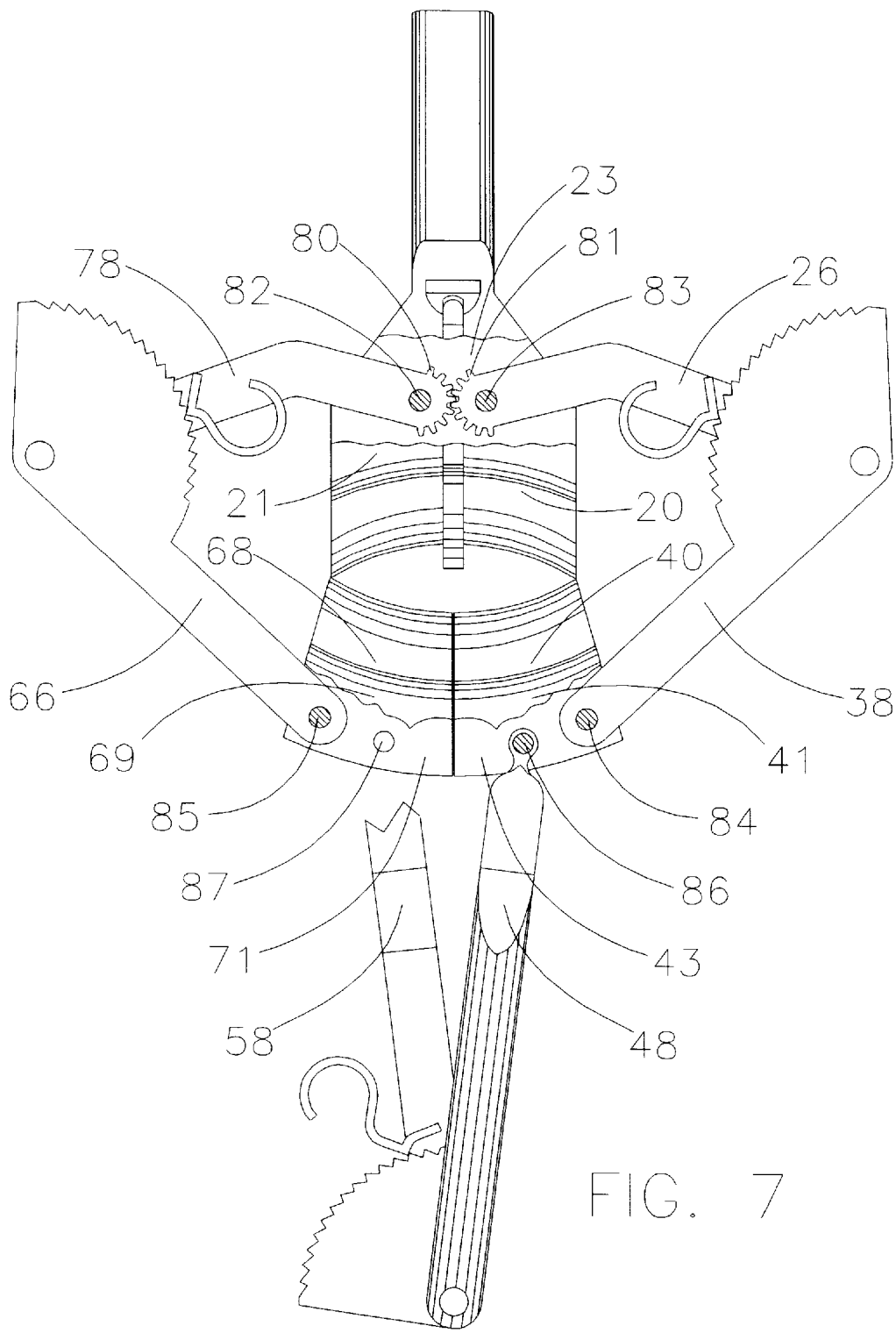
FIG. 7 shows a frontal view of the speculum of FIG. 4, with partial sectional views of the front faces of the top, left, and right blades.

FIGS. 1, 2, 4, and 5 also show that a right ball-and-socket joint 64 is composed of a ball and a socket. The "ball" is a ball portion of the right leg support 60. The socket is formed from a cutaway section of the anterior face of the right blade 62 just anterior and inferior to the ball portion of the right leg support 60 as well as a depression in the posterior face of the right blade 87 just posterior to the ball portion of the right leg support 60 (FIG. 7). This not only allows the ball portion 60 (and thus the right leg support 58 itself) to rotate medially and laterally in the plane between the anterior and posterior faces, but also allows the ball portion of the right leg support 60 to rotate anteriorly (FIG. 6). Thus the right leg support 58 can pivot in the direction of the arrow in FIG. 6 to a position 58'.

FIG. 7 shows partial cross-sections of the anterior faces of the top blade 21, the left blade 41, and the right blade 69.

The partial cross-section of the anterior face of the top blade 21 shows that the medial portion of the left upper arm support 26 is attached to the anterior face 21 and posterior face 23 by a peg 83 that allows support 26 to rotate about it freely. The medial end of the right upper arm support 78 is attached to the anterior face 21 and posterior face 23 by a peg 82 that allows support 78 to rotate about it freely. The medial portion of support 26 also ends in a series of gear teeth 81 that engage a series of gear teeth 80 at the medial portion of support 78. This arrangement requires that supports 26 and 78 rotate symmetrically about the vertical midline of the speculum.

The partial cross-section of the anterior face of the left blade 41 shows that the medial portion of the left lower arm support 38 is connected to the anterior face 41 and posterior face 43 by a peg 84. This peg 84 is permanently attached to face 41, face 43, and support 38 so that no motion is allowed at this junction. A partial cross-sectional view of a ball portion of the left leg support 86 is also illustrated.

The partial cross-section of the anterior face of the right blade 69 shows that the medial portion of the right lower arm support 66 is connected to the anterior face 69 and posterior face 71 by a peg 85. This peg 85 is permanently attached to face 69, face 71, and support 66 so that no motion is allowed at this junction. The superior portion of the right leg support 58 is cut away to allow a depression of the posterior face of the right blade 87, into which the ball portion of the right leg support 60 sits, to be seen.

Illumination System

Attached to the superior portions of the anterior face 21 and posterior face 23 is a hollow light source receptacle 22, slightly posteriorly angulated, into which a commercially available light source 24 is inserted. At the lower end of this receptacle 22 is a curved plastic track 32 that extends from the receptacle 22 through and around the anterior face 21 until it is curved and directed posteriorly. The end of the curved plastic track 32 closest to the receptacle 22 has a surface that is generally hemispherical in shape that helps to focus the light from the light source 24. During the use of the speculum, the light source 24 is positioned in the receptacle 22 and turned on. The light emanating from the light source 24 is then directed by means of the curved plastic track 32 into the cavity created by blades 20, 40, and 68.

Handles

The light receptacle 22 also functions as the upper handle of the speculum while the left leg support 48 and right leg support 58 connected at the hinge joint 52 function as the lower handle.

Figure 8:
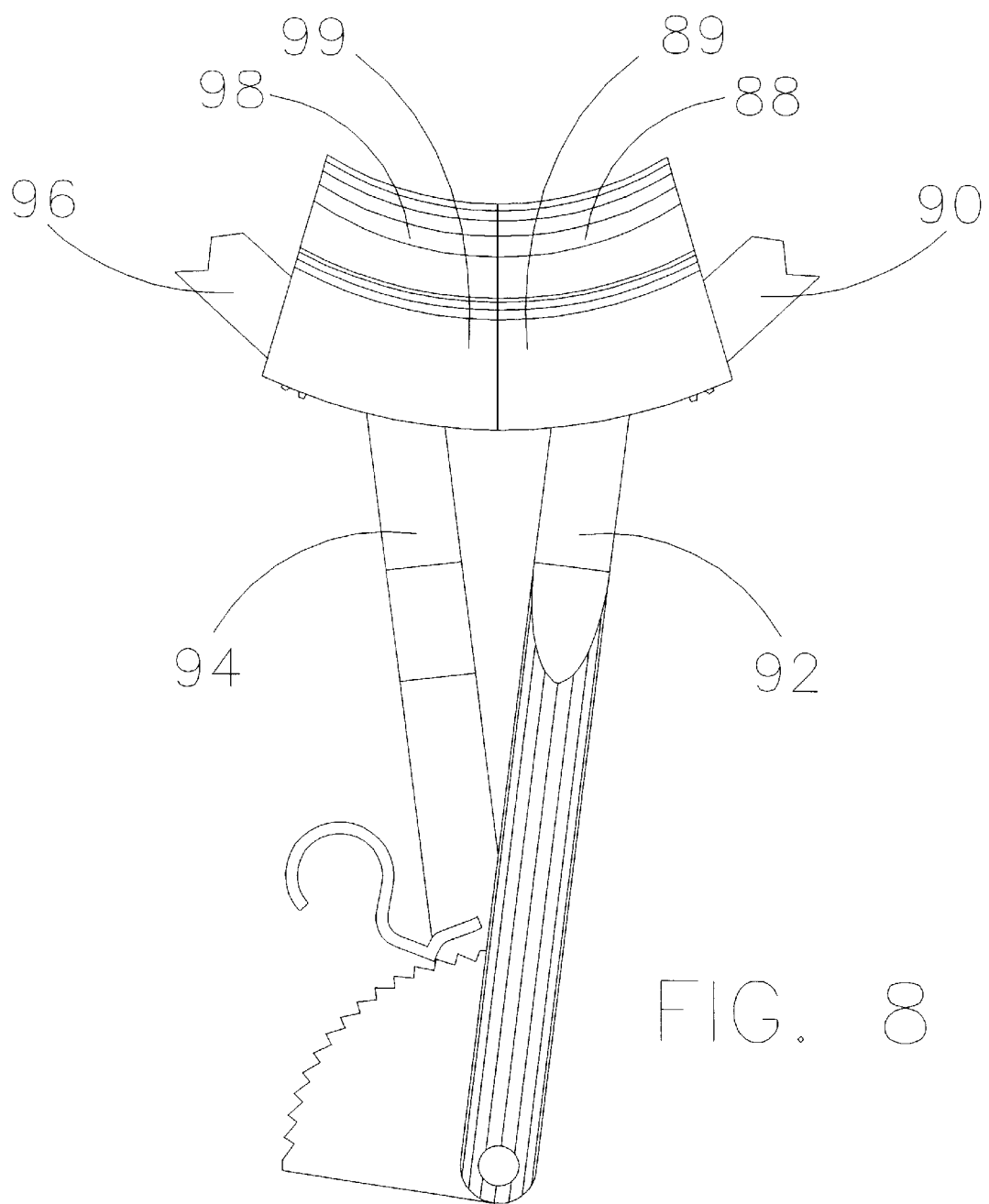
FIG. 8 is a frontal view of an alternative embodiment of the leg supports, the anterior and posterior faces of the left and right blades, and the medial portions of the left and right lower arm supports.
Figure 9:
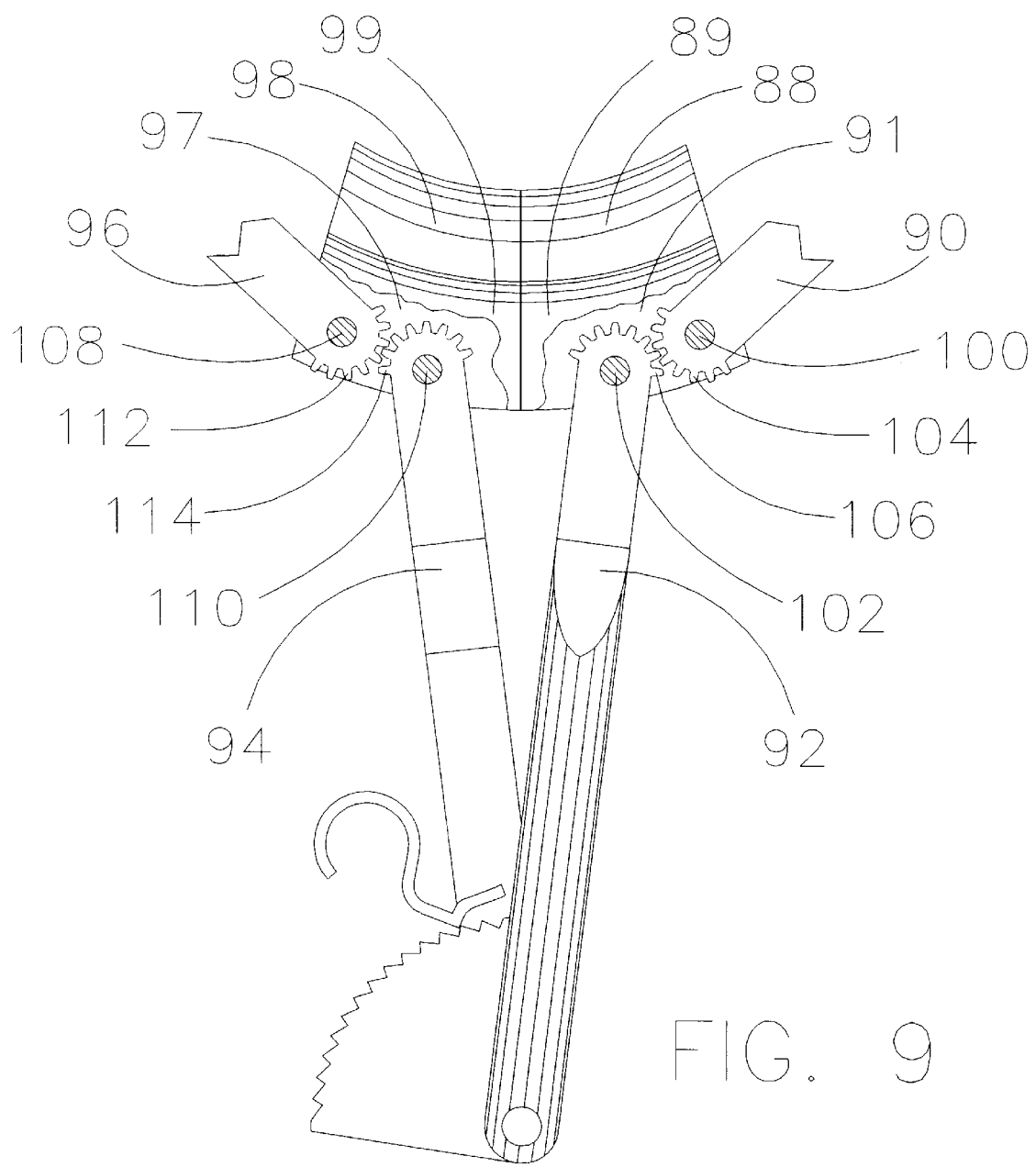
FIG. 9 is a partial sectional view of the front faces of the left and right blades from FIG. 8.

Description of the Alternative Embodiment—FIGS. 8 and 9

FIG. 8 shows a frontal view of an alternative embodiment of a left lower arm support 90, a right lower arm support 96, a left blade 88 and an anterior face of left blade 89, a right blade 98 and an anterior face of the right blade 99, a left leg support 92, and a right leg support 94.

FIG. 9 shows partial cross-sectional views of the alternate anterior faces of the left blade 89 and the right blade 99 from FIG. 8.

In this alternative embodiment, the medial end of the left lower arm support 90 is attached to the anterior face 89 and a posterior face 91 by a peg 100 that allows support 90 to rotate about it freely. The superior end of the left leg support 92 is attached to the anterior face 89 and posterior face 91 by a peg 102 that allows support 92 to rotate about it freely. The medial portion of support 90 also ends in a series of gear teeth 104 that engage a series of gear teeth 106 at the superior portion of the left leg support 92. This arrangement requires that supports 90 and 92 rotate symmetrically about an axis perpendicular to the midpoint of the line between pegs 100 and 102.

Similarly, the medial end of the right lower arm support 96 is attached to the anterior face 99 and a posterior face 97 by a peg 108 that allows support 96 to rotate about it freely. The superior end of the right leg support 94 is attached to the anterior face 99 and posterior face 97 by a peg 110 that allows support 94 to rotate about it freely. The medial portion of support 96 also ends in a series of gear teeth 112 that engage a series of gear teeth 114 at the superior portion of the right leg support 94. This arrangement requires that supports 96 and 94 rotate symmetrically about an axis perpendicular to the midpoint of the line between pegs 108 and 110.

This alternate embodiment, however, will not allow the legs to move toward the operator as in the preferred embodiment.

Operation—FIGS. 1, 4, 10, 11

Figure 10:
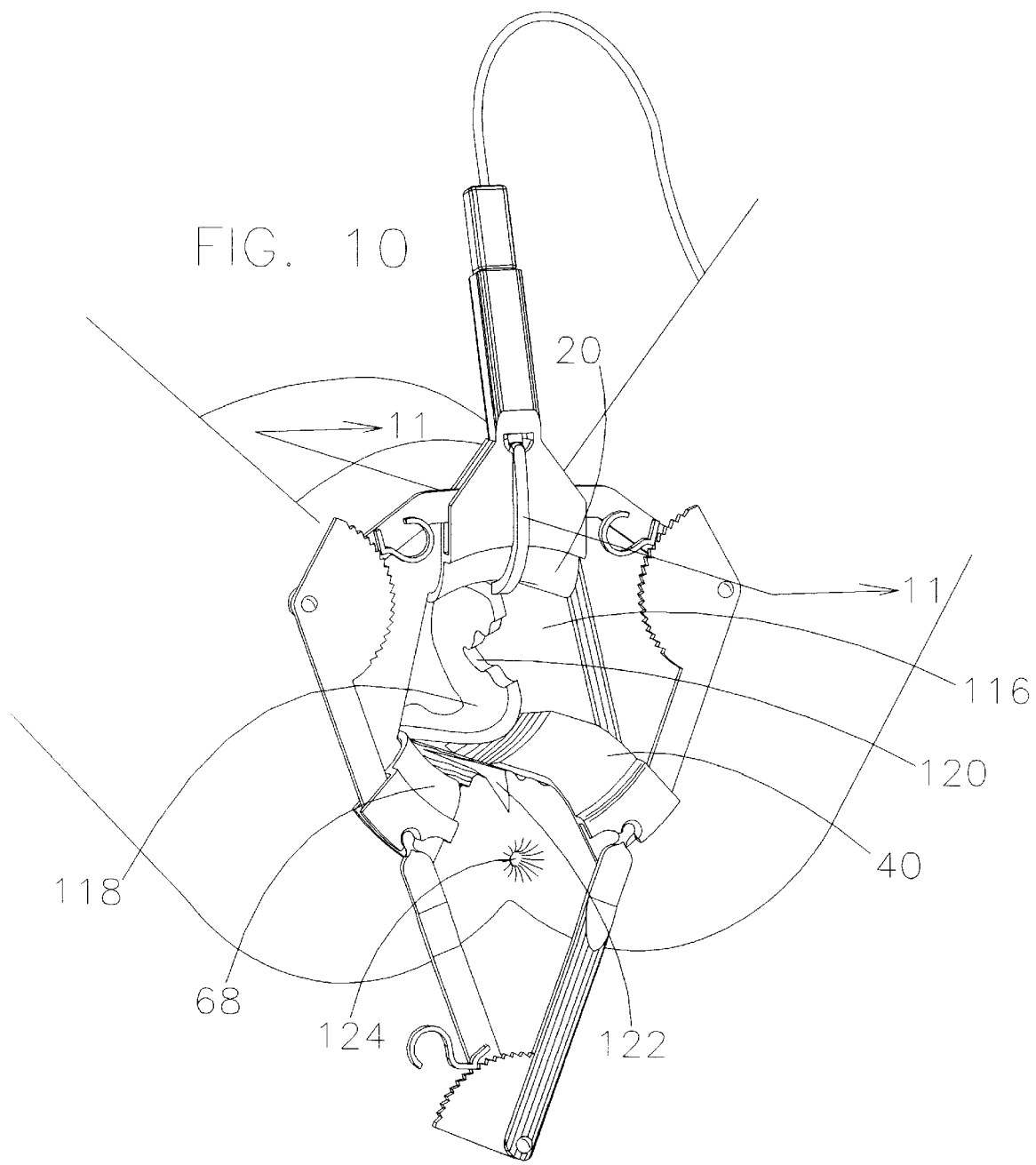
FIG. 10 is a perspective view of what could be seen when the speculum is used in a postpartum situation.
Figure 11:
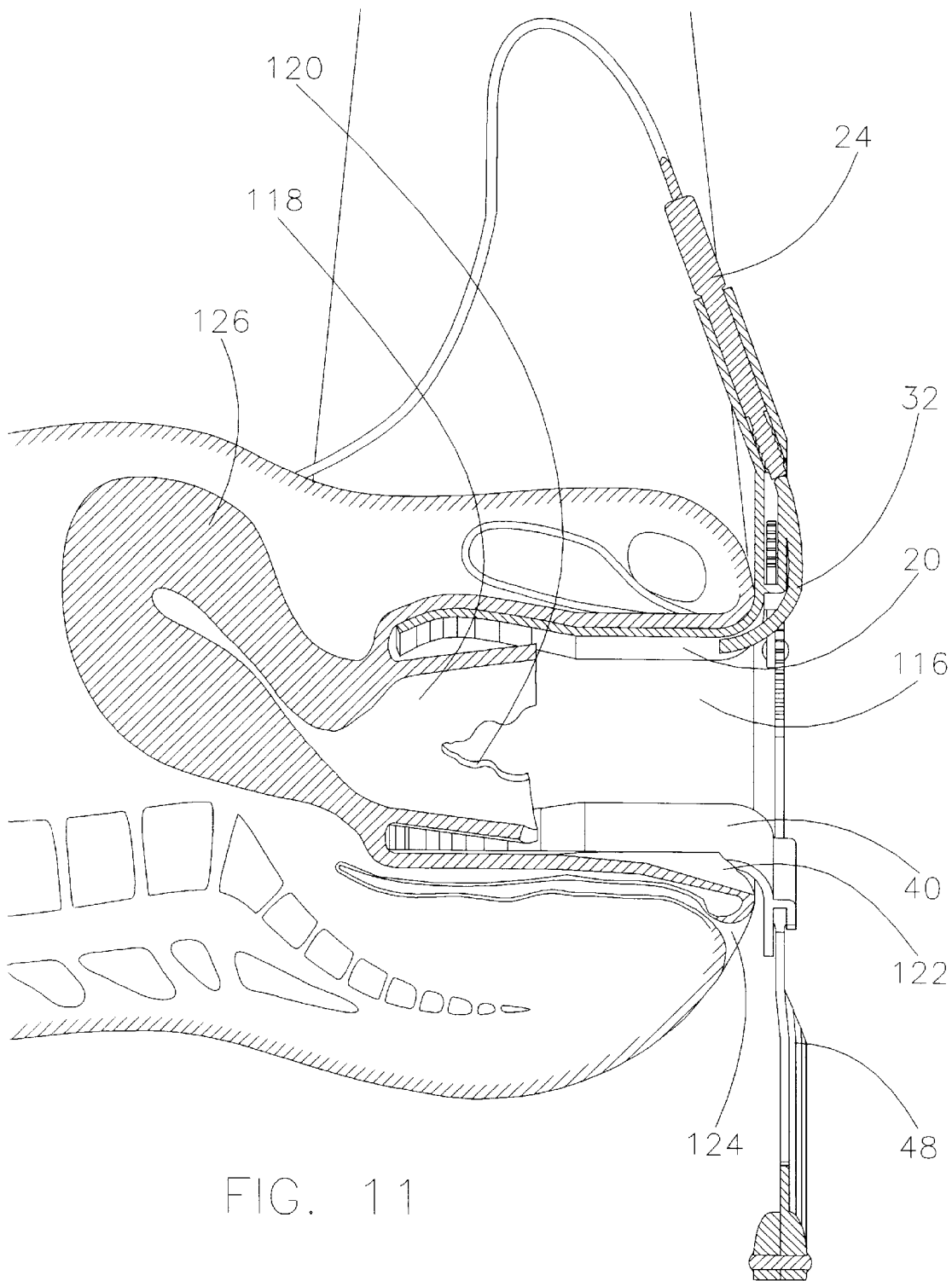
FIG. 11 is a midline section through FIG. 10.

The manner of using the preferred embodiment of this speculum for a postpartum vaginal examination is analogous to that of using a standard speculum for a regular vaginal examination. First, the commercially available light source 24 is turned on and inserted into the hollow light source receptacle 22 by an assistant standing on the opposite side of the supine patient's legs from the operator, on either the patient's left or right side. The cord to the light source is draped on the lower abdomen, anterior to one of the patient's flexed thighs, so as to be away from the operative field (FIGS. 10 and 11).

Then the closed speculum is introduced halfway into the vagina, using the nondominant hand to hold the upper handle of the speculum 22 and the dominant hand grasping the two leg supports 48 and 58 (the lower handle). Care must be taken not to get the speculum inside a dilated cervix 118.

Then with the dominant hand, the two leg supports 48 and 58 are pushed apart so that joint 52 widens and the left blade 40 and the right blade 68 separate, each pushing against a vaginal wall 116. When the two leg supports are no longer being pushed apart, the vaginal wall 116 will exert counter traction against the blades and the supports in such a manner that pawl 55 will engage one rachet tooth 54 and not allow the left leg support 48 and right leg support 58 to move toward each other. At this point, the speculum is inserted as far as it can go, taking care to make sure that the dilated cervix 118 is located inside the cavity formed by the speculum.

If an episiotomy has not been done, the vagina is then preliminarily inspected to identify any vaginal tears. The speculum is then rotated to such a position that a vaginal tear or episiotomy 122 is located directed opposite the center of the top blade 20 and thus between the left blade 40 and right blade 68. If no episiotomy was done and there does not appear to be any vaginal tear, the speculum is then centered with the top blade 20 just under the pubic bone.

Then using the dominant hand, the leg supports 48 and 58 are pulled down, away from nondominant hand holding the upper blade 20 so that the vaginal wall 116 between the upper blade 20 and the left blade 40 and the vaginal wall 116 between the upper blade 20 and the right blade 68 are taut and thus not likely to fall into any operative field. This will also allow the vaginal tissue between the left blade 40 and right blade 68 to be relaxed and allow the opposing walls of a vaginal tissue defect 122 to easily come together to be sutured. When the upper and lower handles are no longer being pulled apart, the vaginal walls will exert counter traction against the blades and the supports so that each of the pawls 33 and 75 will engage one rachet tooth 36 and 70 respectively and thus not allow the left elbow joint 28 and right elbow joint 74 to move or collapse.

If the patient is on a regular bed, without much space between the vagina and the bed, the lower leg supports can be rotated anteriorly, parallel to the bed and still be used as described above (FIG. 6).

Now that the postpartum vagina is completely dilated, the vagina can be fully inspected to see if there are any unknown vaginal tears that may need to be repaired. If need be, the speculum can be rotated so that any tissue obscured by one of the blades can be better visualized. Also the dilated cervix 118 can now be inspected to seen if a cervical tear 120 is present that will need to be repaired or if any residual placental tissue coming out of a contracted uterus 126 will need to be removed.

If any vaginal or cervical defects are found, they can be now be repaired using the techniques that practitioners of the art are well familiar. Also if the vaginal defect extends into the rectum 124, the speculum allows the practitioner ample room to work in this area also.

To remove the speculum, release rings 34 and 76 are simultaneously pulled medially by the index finger and thumb of the nondominant hand, and the release ring 56 is rotated medially by the thumb of the right hand of a right-handed person or the index finger of the left hand of a left-handed person. This two maneuvers may be done in series or concurrently. Again caution needs to be exercised so that the dilated cervix 118 is not caught in the speculum.

The preferred embodiment of the invention and the alternate embodiment can do exactly the same thing with the exception that the leg supports cannot rotate anteriorly in the alternate embodiment. The preferred embodiment can be used with the postpartum patient in regular bed since the leg supports can be flexed toward the operator so as not to get in the way, making it easier for the patient and the operator.

Summary, Ramifications, and Scope

Accordingly, the reader will see that the multi-bladed speculum of the present invention can be used to dilate a body cavity such as a postpartum vagina and assist in the examination, diagnosis, and treatment of conditions associated with the postpartum state much easier, faster, and more accurately than the way practitioners of the art do it presently.

Furthermore the multi-bladed speculum has the additional advantages in that it is simple to use;

it can dilate a body cavity quickly;

it will decrease the overall time for inspection and diagnosis of body cavities such as the postpartum vagina as well as any surgical procedures that may need to be done;

it will allow operations to be done not only on the walls of the body cavity as well as the interior of the body cavity, but also on the surface of the body near the body cavity since the speculum ordinarily will not obstruct this area;

it can be manipulated into an almost limitless number of configurations;

it has a mechanism to channel light directly into the interior of the body cavity;

it is self-retaining in the body cavity that is being dilated;

it is made of a plastic material that is comfortable temperature-wise to the skin or mucous membranes of a conscious patient;

it is disposable, thus not needing sterilization;

it is diverged by applying forces directly to the blades to retract the walls of the body cavity;

it eliminates the need for additional retractors;

it is suited for use with other surgical instruments;

it has a tissue spreading mechanism that can stretch the walls of the body cavity that don't need to be operated on, while allowing the portions of the walls that do, to be relaxed; and it can be used with a patient in any position especially as it relates to postpartum examination either on a delivery table in an operating suite with feet in stirrups or lying in a regular bed.

Although the description above contains many specificities, these should not be construed as limiting the scope of the invention but as merely providing illustrations of some of the presently preferred embodiments of this invention. Many other variations are possible. For example, the speculum can have four, five, or more blades;

have blades of differing shapes and angulations;

have many more supporting arms of differing shapes and angulations;

have different rachet mechanisms to keep the supporting arms apart;

have different gear arrangements between supporting arms;

have the pegs integral to the arm supports;

have different mechanisms to connect the supporting arms to the anterior and posterior faces of the blades;

have different positions for the light receptacle and light source;

have multiple light sources;

dilate other body cavities than the postpartum vagina;

be of a totally different size depending on the body cavity being dilated;

be used as a retractor in many other operative settings such as intra-abdominal operations, vaginal hysterectomies, etc.; and be made of other materials than a clear hard plastic.

Thus the scope of the invention should be determined by the appended claims and their legal equivalents, rather than by the examples given.

What is claimed is:

1. A speculum comprising:

(a) an upper blade, a left lower blade, and a right lower blade each having a distal end, a proximal end, and a convexly curved outer surface extending between the proximal and distal ends, each having a longitudinal axis generally parallel to the others;

(b) a left upper arm having a first end pivotally connected to the proximal end of the upper blade, and a right upper arm having a first end pivotally connected to the proximal end of the upper blade;

(c) a left lower arm having a first end pivotally connected to a second end of the left upper arm and a second end connected to the proximal end of the left lower blade, and a right lower arm having a first end pivotally connected to a second end of the right upper arm and a second end connected to the proximal end of the right lower blade;

(d) a left lower handle member having an upper end pivotally connected to the proximal end of the left lower blade, and a right lower handle member having an upper end pivotally connected to the proximal end of the right lower blade and a lower end pivotally connected to a lower end of the left lower handle member; and (e) a first pawl and ratchet mechanism joining the left upper arm and the left lower arm, a second pawl and ratchet mechanism joining the right upper arm to the right lower arm, and a third pawl and ratchet mechanism joining the left and right lower handle members.

2. The speculum of claim 1 wherein the second end of the left lower arm is rigidly connected to the proximal end of the left lower blade, and the second end of the right lower arm is rigidly connected to the proximal end of the right lower blade.

3. The speculum of claim 1 wherein the second end of the left lower arm is pivotally connected to the proximal end of the left lower blade, and the second end of the right lower arm is pivotally connected to the proximal end of right lower blade, and wherein the left lower handle member includes a first set of gear teeth disposed on its upper end, the left lower arm includes a second set of gear teeth on its second end meshing with the first set of gear teeth, the right lower handle member includes a third set of gear teeth disposed on its upper end, and the right lower arm includes a fourth set of gear teeth meshing with the third set of gear teeth.

4. The speculum of claim 1 including an upper handle connected to the proximal end of the upper blade.

5. The speculum of claim 4 including a light receptacle in the upper handle, and a light guide adapted to guide light from the light receptacle into a cavity defined by inner surfaces of the upper blade, left lower blade, and right lower blade.

6. The speculum of claim 1 wherein the first pawl and ratchet mechanism is adapted to permit increasing of a first angle between the left upper arm and the left lower arm as the speculum is opened and to prevent decreasing of the first angle, and the second pawl and ratchet mechanism is adapted to permit increasing of a second angle between the right upper arm and the left lower arm as the speculum is opened and to prevent decreasing of the second angle.

7. The speculum of claim 6 wherein the third pawl and ratchet mechanism is adapted to permit increasing of a third angle between the right and left lower handle members as the speculum is opened and to prevent decreasing of the third angle.

8. The speculum of claim 7 wherein each of the first, second, and third pawl and ratchet mechanisms includes a spring-biased pawl engaging teeth of a ratchet.

9. The speculum of claim 8 wherein each of the first, second, and third pawl and ratchet mechanisms includes a release feature.

10. The speculum of claim 9 wherein the release feature includes a spring-biased portion of a pawl adapted to permit the pawl to be withdrawn from engagement with ratchet teeth.

11. The speculum of claim 1 wherein the proximal ends of the first, second, and third blades lie in a common plane.

12. The speculum of claim 1 wherein the first, second, and third blades are comprised of hard plastic.

13. The speculum of claim 1 wherein the left upper arm and the right upper arm each includes a plurality of gear teeth disposed on its first end, respectively, engaged with the gear teeth of the other to cause the left and right upper arms to maintain the same angular relationship to the upper blade.

14. The speculum of claim 7 wherein lowering of the left lower handle member and the right lower handle member causes the first and second angles to increase.

15. The speculum of claim 14 wherein increasing the third angle between the left lower handle member and the right lower handle member increases the angle between the left upper arm and the right upper arm.

16. The speculum of claim 11 wherein the pivotal connections of the left lower handle member and the right lower handle member permit pivoting of the left and right lower handle members such that their lower ends can swing out of the common plane in a direction away from the upper, left lower, and right lower blades.

17. A method of dilating a body cavity, comprising:
  (a) inserting an upper blade, a left lower blade, and a right lower blade into the cavity, each blade having a distal end, a proximal end, and a convexly curved outer surface extending between the proximal and distal ends, each having a longitudinal axis generally parallel to the others, so that inner surfaces of the blades define a minimum volume region;
  (b) providing
    i. a left upper arm having a first end pivotally connected to the proximal end of the upper blade, and a right upper arm having a first end pivotally connected to the proximal end of the upper blade,
    ii. a left lower arm having a first end pivotally connected to a second end of the left upper arm and a second end connected to the proximal end of the left lower blade, and a right lower arm having a first end pivotally connected to a second end of the right upper arm and a second end connected to the proximal end of the right lower blade,
    iii. a left lower handle member having an upper end pivotally connected to the proximal end of the left lower blade, and a right lower handle member having an upper end pivotally connected to the proximal end of the right lower blade and a lower end pivotally connected to a lower end of the left lower handle member;
  (c) lowering the left lower blade and the right lower blade relative to the upper blade and spreading the left lower blade and the right lower blade apart to increase the volume of the region defined by the blades; and
  (d) preventing the blades from collapsing toward each other by means of a first pawl and ratchet mechanism joining the left upper arm and the left lower arm, a second pawl and ratchet mechanism joining the right upper arm to the right lower arm, and a third pawl and ratchet mechanism joining the left and right handle members.

18. The method of claim 17 including performing the lowering of step (c) by means of an upper handle connected to the proximal end of the upper blade and by means of one of the lower handle members, and performing the spreading of step (c) by means of the left and right lower handle members.

19. The method of claim 18 including providing a light receptacle in the upper handle, and guiding light from the light receptacle into the region defined by inner surfaces of the upper blade, left lower blade, and right lower blade.

20. The method of claim 17 including releasing the first, second, and third pawl and ratchet mechanisms to allow the blades to collapse toward each other, and withdrawing the blades from the cavity.

21. The method of claim 17 wherein the proximal ends of the first, second, and third blades lie in a common plane, the method including pivoting the left and right lower handle members away from the common plane.

22. A speculum comprising:
  (a) a first blade, a second blade, and a third blade each having a distal end, a proximal end, and a convexly curved outer surface extending between the proximal and distal ends, each having a longitudinal axis generally parallel to the others;
  (b) an expandable and collapsible support ring including a plurality of members pivotally connected end-to-end and including
    i. a first arm having a first end pivotally connected to the proximal end of the first blade, and a second arm having a first end pivotally connected to the proximal end of the first blade,
    ii. a third arm having a first end pivotally connected to a second end of the first arm and a second end connected to the proximal end of the second blade, and a fourth arm having a first end pivotally connected to a second end of the second arm and a second end connected to the proximal end of the third blade; and
  (c) a first pawl and ratchet mechanism joining the first arm and the third arm, a second pawl and ratchet mechanism joining the second arm to the fourth arm.

23. The speculum of claim 22 wherein the support ring includes a first handle member having first end pivotally connected to the proximal end of the second blade, and a second handle member having a first end pivotally connected to the proximal end of the third blade and a second end pivotally connected to a second end of the first handle member and a third pawl and ratchet mechanism joining the first and second handle members.

24. The speculum of claim 22 wherein the second end of the left lower arm is rigidly connected to the proximal end of the left lower blade, and the second end of the right lower arm is rigidly connected to the proximal end of the right lower blade.

25. The speculum of claim 22 wherein the second end of the left lower arm is pivotally connected to the proximal end of the left lower blade, and the second end of the right lower arm is pivotally connected to the proximal end of right lower blade, and wherein the left lower handle member includes a first set of gear teeth disposed on its upper end, the left lower arm includes a second set of gear teeth on its second end meshing with the first set of gear teeth, the right lower handle member includes a third set of gear teeth disposed on its upper end, and the right lower arm includes a fourth set of gear teeth meshing with the third set of gear teeth.

26. The speculum of claim 22 wherein the proximal ends of the first, second, and third blades lie in a common plane, and wherein the pivotal connections of the left lower handle member and the right lower handle member permit pivoting of the left and right lower handle members such that their lower ends can swing out of the common plane in a direction away from the upper, left lower, and right lower blades.

* * * * *